United States Patent
Nair et al.

(10) Patent No.: US 10,005,705 B2
(45) Date of Patent: *Jun. 26, 2018

(54) PROCESS FOR THE PRODUCTION OF FLUORINATED CYCLOBUTANE

(71) Applicant: Honeywell International Inc., Morris Plains, NJ (US)

(72) Inventors: Haridasan K. Nair, Williamsville, NY (US); Rajiv Banavali, Morristown, NJ (US); Yian Zhai, Lockport, NY (US); Glenn Matthies, Lockport, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/807,033

(22) Filed: Nov. 8, 2017

(65) Prior Publication Data

US 2018/0065905 A1     Mar. 8, 2018

Related U.S. Application Data

(63) Continuation of application No. PCT/US2017/060394, filed on Nov. 7, 2017, and a continuation-in-part of application No. 15/582,981, filed on May 1, 2017, now Pat. No. 9,856,193, which is a continuation-in-part of application No. 15/345,695, filed on Nov. 8, 2016, now Pat. No. 9,790,151.

(60) Provisional application No. 62/254,338, filed on Nov. 12, 2015.

(51) Int. Cl.
C07C 17/275        (2006.01)

(52) U.S. Cl.
CPC ........ *C07C 17/275* (2013.01); *C07C 2601/04* (2017.05)

(58) Field of Classification Search
CPC .... C07C 17/272; C07C 17/361; C07C 17/383
See application file for complete search history.

(56) References Cited

U.S. PATENT DOCUMENTS

| | | |
|---|---|---|
| 2,427,116 A | 9/1947 | Barrick |
| 2,441,128 A | 5/1948 | Barrick et al. |
| 2,462,345 A | 2/1949 | Barrick |
| 2,848,504 A | 8/1958 | Dixon |
| 2,931,840 A | 4/1960 | Marquis |
| 2,982,786 A | 5/1961 | Mccane |
| 3,996,299 A | 12/1976 | Fozzard |
| 3,996,301 A | 12/1976 | Fozzard |
| 4,086,407 A | 4/1978 | Fozzard |
| 5,026,499 A | 6/1991 | Merchant |
| 5,035,830 A | 7/1991 | Merchant |
| 6,624,337 B1 | 9/2003 | Manzer et al. |
| 7,674,939 B2 | 3/2010 | Mukhopadhyay et al. |
| 8,058,486 B2 | 11/2011 | Merkel et al. |
| 8,084,653 B2 | 12/2011 | Tung et al. |
| 8,324,436 B2 | 12/2012 | Mukhopadhyay et al. |
| 8,425,795 B2 | 4/2013 | Nappa et al. |
| 8,618,340 B2 | 12/2013 | Kopkalli et al. |
| 8,975,454 B2 | 3/2015 | Merkel et al. |
| 9,061,957 B2 | 6/2015 | Mukhopadhyay et al. |
| 9,790,152 B2 | 10/2017 | Sharratt et al. |
| 9,856,193 B2 | 1/2018 | Nair et al. |
| 2008/0058562 A1 | 3/2008 | Petrov et al. |
| 2009/0099396 A1 | 4/2009 | Mukhopadhyay et al. |
| 2009/0186986 A1 | 7/2009 | Nomura et al. |
| 2011/0097529 A1 | 4/2011 | Durali et al. |
| 2014/0147480 A1 | 5/2014 | Lu et al. |
| 2014/0179887 A1 | 6/2014 | Lu et al. |
| 2017/0137353 A1 | 5/2017 | Banavali et al. |
| 2017/0233316 A1 | 8/2017 | Nair et al. |

FOREIGN PATENT DOCUMENTS

| | | |
|---|---|---|
| JP | 2012188359 A | 10/2012 |
| KR | 1020110093831 A | 8/2011 |
| WO | WO0075092 A1 | 12/2000 |
| WO | 2006011868 A1 | 2/2006 |
| WO | 2009003085 A1 | 12/2008 |
| WO | WO 2009/003085 A1 * | 12/2008 |
| WO | 2010055146 A2 | 5/2010 |

OTHER PUBLICATIONS

Birchall, Michael J., et al. "Cyclopropane Chemistry. Part III. Thermal Decomposition of Some Halogenopolyfluorocyclopropanes." Journal of the Chemical Society, Perkin Transactions 1: Organic and Bio-Organic Chemistry, 16:1773-1779, 1973.
Haszeldine, Robert N., et al. "Preliminary Note: Reaction of Hexafluoropropene With Halogenoalkanes." Journal of Fluorine Chemistry, 21:253-259, 1982.
Hauptschein, Murray, et al. "The Thermal Dimerization of Perfluoropropene." Contribution from the Organic Research Department, Pennsalt Chemicals Corp., vol. 80, pp. 842-845, Feb. 20, 1958.
International Search Report and Written Opinion issued in PCT/US2016/061021, dated Jan. 17, 2017, 7 pages.
Placzek, D. W. and Rabinovitch, B.S. "The Thermal Isomerization of Trifluoromethyl- and Trifluoroethylcyclopropane." The Journal of Physical Chemistry, 69(7):2141-2145, Jul. 2015, 1965.
Sakaino, Yoshiko. "Structures and Chromotropic Properties of Imadazole Derivatives Produced from 3,6-Bis(4,5-diphenyl-2H-imidazol-2-ylidene)cyclohexa-1,4-diene." J. Chem. Soc. Perkin Trans. I, pp. 1063-1066, 1983.
Solvay Solexis, Via S. Pietro. "2Pi Plus 2Pi Cycloaddition Kinetics of Some Fluoro Olefins and Fluoro Vinyl Ethers." Elsevier, Journal of Fluorine Chemistry, 125:1519-1528, 2004.
Stoiljkovich, D. and Jovanovich, S. "The Mechanism of the High-Pressure Free Radical Polymerization of Ethylene." Journal of Polymer Science: Polymer Chemistry Edition, vol. 19, 741-747, 1981.
International Search Report and Written Opinion issued in PCT/US2017/060394, dated Feb. 14, 2018, 11 pages.

* cited by examiner

*Primary Examiner* — Jafar Parsa
(74) *Attorney, Agent, or Firm* — Faegre Baker Daniels LLP (57) ABSTRACT

The production of 1,1,2-trifluoro-2-(trifluoromethyl)cyclobutane (TFMCB). More specifically, the present invention relates to a process for making 1,1,2-trifluoro-2-(trifluoromethyl)cyclobutane via a continuous catalytic reaction from commercially available raw materials ethylene and hexafluoropropene.

20 Claims, 1 Drawing Sheet

PROCESS FOR THE PRODUCTION OF FLUORINATED CYCLOBUTANE

CROSS-REFERENCE TO RELATED APPLICATIONS

This application is a continuation application of International Application No. PCT/US2017/060394, filed Nov. 7, 2017, and is also a continuation-in-part application of U.S. patent application Ser. No. 15/582,981, filed May 1, 2017, which is a continuation-in-part of U.S. patent application Ser. No. 15/345,695, filed on Nov. 8, 2016, now U.S. Pat. No. 9,790,151, issued Oct. 17, 2017, which claims the benefit under Title 35, U.S.C. § 119(e) of U.S. Provisional Patent Application Ser. No. 62/254,338, filed on Nov. 12, 2015, and the entire disclosures of each of the foregoing applications are expressly incorporated by reference herein.

FIELD OF THE INVENTION

The present invention relates to the production of 1,1,2-trifluoro-2-(trifluoromethyl)cyclobutane (TFMCB). More specifically, the present invention relates to methods for production of 1,1,2-trifluoro-2-(trifluoromethyl)cyclobutane via a continuous catalytic reaction from commercially available reactants ethylene and hexafluoropropene.

BACKGROUND

The hydrofluoro-olefin 2,3,3,3-tetrafluoropropene (HFO-1234yf, $CF_3CF=CH_2$) is a low global warming compound with zero ozone depletion potential which finds use as a refrigerant, a foam blowing agent, a monomer for polymers, and many other applications. A number of methods are known in the art for making HFO-1234yf. See, for example U.S. Pat. Nos. 8,975,454, 8,618,340, 8,058,486, and 9,061,957. See also, U.S. Patent Pub. Nos. 2009-0099396 and 2008-0058562.

Another route to HFO-1234yf is the hydrofluorination of 1,1,2,3-tetrachloro-propene (TCP), as disclosed in U.S. Pat. Nos. 8,084,653 and 8,324,436. PCT Publication WO 2009/003085 A1 describes the preparation of HFO-1234yf via the metathesis of hexafluoropropene (HFP) and ethylene. This process requires the use of an expensive metathesis catalyst in an organic solvent and thus not cost effective for commercial production.

These methods for making HFO-1234yf generally involve multiple steps, by-product formation, and have a low atom efficiency percentage. Atom efficiency percentage is calculated as follows:

(the molecular weight of the desired product)divided by(the molecular weight of the substances formed)×100.

The thermal dimerization of fluoro-olefins has been described in the literature. See, for example, U.S. Pat. Nos. 2,427,116; 2,441,128; 2,462,345; 2,848,504; 2,982,786; and 3,996,301. See also, J. Fluorine. Chem., 2004, 125, 1519; J. Chem. Soc., Perkin I, 1973, 1773; J. Chem. Soc., Perkin I, 1983, 1064.

U.S. Pat. No. 3,996,299 describes a process for the formation of the copolymer produced from vinylidine fluoride and 2,3,3,3-tetrafluoro-propylene. This process involves the cyclodimerization of a perfluoroolefin, such as perfluoropropylene, with a terminal monoolefin, such as ethylene, to produce the cyclic compound 1,1,2-trifluoro-2-trifluoromethyl-cyclobutane (TFMCB). The cyclic compound such as TFMCB is then subjected to a thermal cracking operation to produce a mixture of acyclic fluorine-containing olefins, such as vinylidine fluoride and 2,3,3,3-tetrafluoro-propylene, which can be used as monomers and/or comonomers in polymerization reactions.

The '299 patent discloses the cyclodimerization reaction can occur over a very wide range of reaction conditions. For example, the patent indicates that the reaction temperature can be in the range of 200°-600° C., preferably 300°-400° C., and that the reaction time in the range of about 4 to about 1000 hours, preferably 10 to 100 hours. The '299 patent also indicates that the ratio of the monoolefin to the perfluoroolefin usually is in the range of 0.1:1 to about 100:1 preferably 1:1 to about 10:1.

The '299 patent discloses that the thermal cracking of the cyclic compound at temperatures in the range of 500° to 1000° C. and preferably in the range of 600° to 700° C. It is stated that the cracking reaction can be carried out continuously by passage through a heated reactor tube maintaining a contact time in the range of 0.01-10 seconds.

Applicants have come to recognize several problems and disadvantages associated with the formation of HFO-1234yf according to a process as described in the '299 patent. One such problem is that the '299 patent fails to recognize the potential problem in the cracking reaction associated with olefin oligomerization at high temperatures. Other problems are the presence of HFP and ethylene (the starting material) in the cracking products along with other side products, which are not mentioned in the '299 patent. Applicants have come to appreciate that these problems would be exacerbated under many of the cyclodimerization reaction conditions specified in the '299 patent. The final reaction product is thus a complex mixture under the specified reaction conditions, especially with large excess of ethylene to HFP ratios. Another problem is that many of the permitted ratios of perfluoroolefin, such as HFP, to the monolefin, such as ethylene, can produce undesirable reaction product results, including unwanted or detrimental by-products and/or poor conversions and/or selectivities. Similar disadvantages associated with unwanted or detrimental by-products and/or poor conversions and/or selectivities are possible within the range of reaction conditions for the cracking reaction.

At least in part as a result of the recognition of these problems with the prior art, applicants have developed new and greatly improved processes that provide significant and unexpected advantages in the production of HFO-1234yf and mixtures of HFO-1234yf and vinylidine fluoride (VDF).

In view of the above, fluorinated cyclobutane, specifically 1,1,2-trifluoro-2-(trifluoromethyl)cyclobutane (hereinafter referred as TFMCB) is potentially a very useful intermediate that can converted to hydrofluoroolefin 1234yf ($CF_3CF=CH_2$, 2, 3, 3, 3-tetrafluoropropene) and vinylidene fluoride (VDF, $CH_2=CF_2$) in high yields by pyrolysis according to the method disclosed in U.S. patent application Ser. No. 15/345,695, assigned to the assignee of the present invention, the disclosure of which is expressly incorporated herein by reference.

The chemical structure of TFMCB is shown below:

1,1,2-trifluoro-2-(trifluoromethyl)cyclobutane (TFMCB)

1234yf is commercially available from Honeywell International Inc. under the trademark Solstice™. Both 1234yf and VDF are commercially important compounds, specifically, 1234yf is a low global warming compound with zero ozone depletion potential useful as a refrigerant, foam blowing agent, monomer for polymers and many other applications, and VDF is a monomer useful for producing polymers, such as polyvinylidene fluoride (PVDF).

TFMCB is a known compound having a boiling point of 68° C. TFMCB was used as a component of a cleaning solvent composition in U.S. Pat. Nos. 5,026,499 and 5,035,830, which are incorporated herein by reference. Methods for the synthesis of TFMCB are known. For example, PCT Publication No. 2000/75092, which is incorporated herein by reference, describes the codimerization of TFE and ethylene to give tetrafluorocyclobutane, and subsequent electrochemical fluorination to give perfluorocyclobutanes.

However, methods for producing TFMCB are very few. Birchall, M. et. al., (J. Chem. Soc. 1973, 1773-1779) describes the formation of TFMCB by the reaction of hexafluoropropene (HFP) and ethylene at 250° C. for 18 hours in a rocking autoclave. Haszeldine et. al., (J. Fluorine Chem. 1982, 21, 253-260) reports TFMCB as one of the by-products in the reaction of hexafluoropropene and ethyl chloride at 280° C. for 4 days. U.S. Pat. Nos. 3,996,299 and 4,086,407 describe the generation of 1,1,2-trifluoro-2-(trifluoromethyl) cyclobutane by heating hexafluoropropene and ethylene in a closed stainless steel cylinder at 350° C. for about 3 days.

None of the foregoing methods are cost effective and amenable to practice at a large, commercial scale. Thus, there is a need to develop commercially feasible methods for producing TFMCB.

SUMMARY OF THE INVENTION

The present invention relates to the production of 1,1,2-trifluoro-2-(trifluoromethyl)cyclobutane (TFMCB), and provides methods for producing 1,1,2-trifluoro-2-(trifluoromethyl)cyclobutane via a continuous catalytic reaction from commercially available raw materials ethylene and hexafluoropropene.

In one form thereof, the present invention provides a continuous process for producing 1,1,2-trifluoro-2-(trifluoromethyl)cyclobutane (TFMCB), including the following steps: (a) introducing hexafluoropropene and ethylene into a reaction vessel; (b) reacting the hexafluoropropene and ethylene in the reaction vessel in the presence of at least one metal catalyst; (c) removing TFMCB product from the reaction vessel; and (d) repeating said introducing, reacting and removing steps (a) through (c).

The foregoing process may further include the additional steps of removing at least one of unreacted hexafluoropropene and unreacted ethylene from the reaction vessel, and recycling the at least one of unreacted hexafluoropropene and unreacted ethylene back into the reaction vessel. Alternatively, the foregoing process may further include the additional steps of removing unreacted hexafluoropropene and unreacted ethylene from the reaction vessel; and recycling the unreacted hexafluoropropene and unreacted ethylene back into the reaction vessel.

The metal catalyst may include at least one metal catalyst selected from the group consisting of nickel and nickel-based alloys. In the reacting step, at least one of the following conditions may be present: the reaction may be conducted at a pressure between 600 psig and 1500 psig or at a pressure between 800 psig and 1200 psig; the reaction may be conducted at a temperature between 300° C. and 500° C. or at a temperature between 300° C. and 400° C.; and hexafluoropropene and ethylene may be present at a molar ratio of from 1:1 to 1:6 or at a molar ratio of from 1:1 to 1:3.

The reacting step may be carried out in the presence of at least one oligomerization/polymerization (OP) inhibitor selected from the group consisting of catechol and its derivatives, terpenes, quinones and combinations thereof, and/or may be gas phase nitric oxide (NO). The oligomerization/polymerization (OP) inhibitor may be present at from about 50 ppm to about 2,000 ppm by weight based on the total weight of the reaction composition in the reaction vessel or may be present at from about 500 ppm to about 1,000 ppm based on the total weight of the reaction composition in the reaction vessel.

In another form thereof, the present invention provides a continuous process for producing 1,1,2-trifluoro-2-(trifluoromethyl)cyclobutane (TFMCB), including the following steps: (a) introducing hexafluoropropene and ethylene into a reaction vessel; (b) reacting the hexafluoropropene and ethylene in the reaction vessel in the presence of at least one metal catalyst and at least one oligomerization/polymerization (OP) inhibitor; (c) removing TFMCB product from the reaction vessel; and (d) repeating said introducing, reacting and removing steps (a) through (c).

The at least one metal catalyst may include at least one metal catalyst selected from the group consisting of nickel and nickel-based alloys.

The reacting step is carried out in the presence of at least one oligomerization/polymerization (OP) inhibitor selected from the group consisting of catechol and its derivatives, terpenes, quinones and combinations thereof and/or may be gas phase nitric oxide (NO). The oligomerization/polymerization (OP) inhibitor may be present at from about 50 ppm to about 2,000 ppm by weight based on the total weight of the reaction composition in the reaction vessel.

In the foregoing process, at least one of the following conditions may be present during the reacting step: the reacting step may conducted at a pressure between 600 psig and 1500 psig; the reacting step may be conducted at a temperature between 300° C. and 500° C.; and during the reacting step, the hexafluoropropene and ethylene may be present at a molar ratio of from 1:1 to 1:6.

In a further form thereof, the present disclosure provides a process for producing 1,1,2-trifluoro-2-(trifluoromethyl) cyclobutane (TFMCB), including the following steps: introducing hexafluoropropene and ethylene into a reaction vessel; and reacting the hexafluoropropene and ethylene in the reaction vessel in the presence of at least one oligomerization/polymerization (OP) inhibitor and at least one metal catalyst.

The process may be a continuous process and may further include the additional steps, following the reacting step, of: removing TFMCB product from the reaction vessel; and repeating said introducing, reacting and removing steps (a) through (c).

The process may further include the additional steps, following the reacting step, of: removing at least one of unreacted hexafluoropropene and unreacted ethylene from the reaction vessel; and recycling the at least one of unreacted hexafluoropropene and unreacted ethylene back into the reaction vessel.

The process may further include the additional steps, following the reacting step, of: removing unreacted hexafluoropropene and unreacted ethylene from the reaction vessel; and recycling the unreacted hexafluoropropene and unreacted ethylene back into the reaction vessel.

The metal catalyst may be selected from the group consisting of nickel and nickel-based alloys.

The oligomerization/polymerization (OP) inhibitor may include at least one gas phase compound selected from the group consisting of nitric oxide (NO), nitrogen dioxide ($NO_2$), carbon monoxide (CO) and sulphur dioxide ($SO_2$). The oligomerization/polymerization (OP) inhibitor may be 2,2,6,6-tetramethylpiperidinyl-1-oxl. The oligomerization/polymerization (OP) inhibitor may be selected from the group consisting of catechol and catechol derivatives, terpenes, quinones and combinations thereof.

The oligomerization/polymerization (OP) inhibitor may be present at from about 50 ppm to about 2,000 ppm by weight based on the total weight of the reaction composition in the reaction vessel, or may be present at from about 500 ppm to about 1,000 ppm based on the total weight of the reaction composition in the reaction vessel.

The reacting step may be conducted at a pressure between 600 psig and 1500 psig, or at a pressure between 800 psig and 1200 psig. The reacting step may be conducted at a temperature between 300° C. and 500° C., or at a temperature between 300° C. and 400° C. During the reacting step, the hexafluoropropene and ethylene may be present at a molar ratio of from 1:1 to 1:6.

In another form thereof, the present disclosure provides a process for the formation of a mixture of the compounds 2,3,3,3-tetrafluoropropene (1234yf) and vinylidene fluoride, including the step of pyrolyzing 1,1,2-trifluoro-2-trifluoromethyl-cyclobutane (TFMCB), wherein the TFMCB has a purity greater than 92%, under conditions effective to produce a reaction product comprising 1234yf and vinylidene fluoride in a 1234yf:vinylidene fluoride molar ratio of from about 0.5 to about 1.2.

The pyrolysis may be conducted at a temperature in the range of from about 750° C. to about 800° C. and for a contact time of from about 2 seconds to about 25 seconds and at a pressure of about 1 atm.

The pyrolysis may be conducted in a stainless steel tube reactor, and the reaction may be quenched by cooling as the products come out of the reactor.

In a further form thereof, the present disclosure provides a process for the formation of a mixture of the compounds 2,3,3,3-tetrafluoropropene (1234yf) and vinylidene fluoride, including the step of pyrolyzing 1,1,2-trifluoro-2-trifluoro-methyl-cyclobutane under conditions effective to produce a reaction product comprising 1234yf and vinylidene fluoride in a 1234yf:vinylidene fluoride molar ratio of from about 0.5 to about 1.2; wherein the pyrolysis provides a yield in the range of about 80% to about 90%.

The pyrolysis may provide a conversion rate of about 70%. The pyrolysis may be conducted in a batch mode or in a continuous mode.

The method may further include the step of separating the mixture of the compounds 1234yf and vinylidene fluoride.

In a still further form thereof, the present disclosure provides a process for the formation of a mixture of the compounds 2,3,3,3-tetrafluoropropene (1234yf) and vinylidene fluoride, including the step of pyrolyzing 1,1,2-trifluoro-2-trifluoro-methyl-cyclobutane under conditions effective to produce a reaction product comprising 1234yf and vinylidene fluoride in a 1234yf:vinylidene fluoride molar ratio of from about 0.5 to about 1.2; the process further including the step of forming the compound 1,1,2-trifluoro-2-trifluoromethyl-cyclobutane (TFMCB) by the thermal dimerization a mixture of hexafluoro-propene (HFP) and a stoichiometric excess of ethylene, in the presence of a polymerization or oligomerization inhibitor; and wherein the TFMCB has a purity greater than 92%.

The HFP and ethylene may be mixed in a reactor at a molar ratio of from 1:1 to 1:10 or a molar ratio of from 1:1 to 1:6. The inhibitor may present at from about 200 ppm to about 3% by weight, or from about 500 ppm to 5000 ppm. The inhibitor may be selected from the group consisting of catechol and its derivatives, terpenes, quinones and combinations of two or more thereof. The inhibitor may be selected from the group consisting of t-butyl catechol, limonene, pinene, 1,4-naphtho-quinone, 2,5-di-tert-butyl-hydroquinone, hydroquinone, hydroquinone monomethyl ether, mono-tert-butyl hydroquinone, para-benzoquinone, toluhydroquinone, trimethyl-hydroquinone and combinations of any two or more thereof.

The thermal dimerization may be conducted at a temperature in the range of from about 250° C. to 450° C. or the thermal dimerization may be conducted at a temperature in the range of from about 300° to 350° C. The thermal dimerization may be conducted for a reaction time in the range of from about one to five hours, or for a reaction time in the range of from about one to five hours.

In a further embodiment, any unreacted starting materials may be recycled into a separate container, and the product TFMCB may be purified by distillation at greater than 99.8% purity.

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

BRIEF DESCRIPTION OF THE DRAWINGS

The above mentioned and other features of the invention, and the manner of attaining them, will become more apparent and the invention itself will be better understood by reference to the following description of embodiments of the invention taken in conjunction with the accompanying drawings.

Although the drawings represent embodiments of various features and components according to the present disclosure, the drawings are not necessarily to scale and certain features may be exaggerated in order to better illustrate and explain the present disclosure. The exemplification set out herein illustrates an embodiment of the invention, and such exemplification is not to be construed as limiting the scope of the invention in any manner.

DETAILED DESCRIPTION

I. Production of 1,1,2-trifluoro-2-(trifluoromethyl)cyclobutane (TFMCB)

Figure 1:
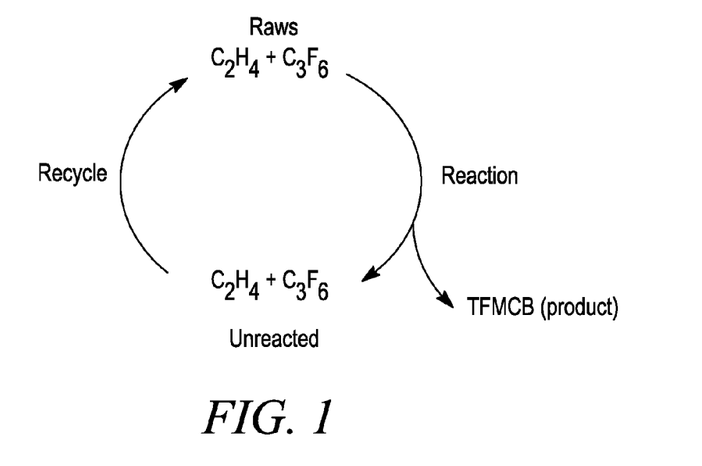
FIG. 1 is a generalized schematic representation of an exemplary process for the production of TFMCB according to the present invention.

Referring to FIG. 1, a method or process is shown for the production of 1,1,2-triflfuoro-2-(trifluoromethyl)cyclobutane (TFMCB). As described further below, the method involves a continuous process in which ethylene ($C_2H_4$) and hexafluoropropene ($C_3F_6$) reactants (i.e., raw materials or "raws") are added continuously or periodically to a reaction vessel as needed, products are removed from the reaction vessel continuously or periodically as needed and optionally purified, and unreacted materials are removed from the reaction vessel continuously or periodically as needed and optionally recycled back into the reaction vessel. In this manner, the reaction is carried out by constant feeding of reactants and removal of product (TFMCB) and recycling unreacted ethylene ($C_2H_4$) and hexafluoropropene.

Conversion of hexafluoropropene to TFMCB and its selectivity is dependent on temperature, pressure, flow rates, reactants ratio, and the use of catalysts and/or polymerization inhibitors.

Although the reactants may be prone to oligomerization/polymerization, as discussed below the present inventors have found that oligomerization/polymerization of the reactants can be controlled, in order to enhance conversion of the reactants to the desired TFMCB product by control of reaction conditions and/or with the use of at least one catalyst and/or at least one oligomerization/polymerization (OP) inhibitor.

Figure 2:
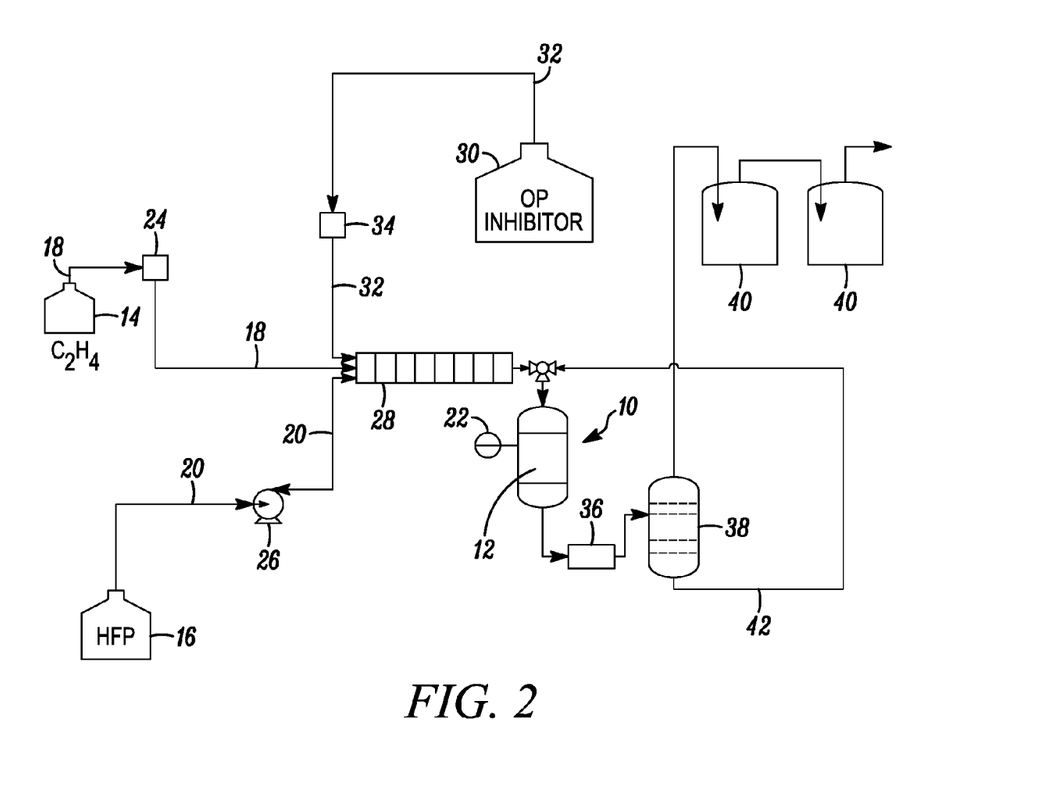
FIG. 2 is a structural schematic including components used in an exemplary process for the production of TFMCB according to the present invention.

Referring to FIG. 2, exemplary components for carrying out the continuous reaction are shown. The reaction itself is carried out in a reaction vessel 10, which may be a heated tube reactor, for example, and which as discussed in further detail below, contains a catalyst 12. The reactants ethylene and hexafluoropropene are fed from respective supply tanks 14 and 16 at desired flow rates via conduits 18 and 20, respectively, to reaction vessel 10. Reaction vessel 10 may be heated by an appropriate heating mechanism, such as by being placed in a furnace or by the use of heating sleeves and/or tapes, and is equipped with an internal temperature sensor 22 to monitor inside temperature. Reaction vessel 10 may be made of stainless steel, nickel, nickel-based alloys such as Monel® (e.g., up to 67% nickel, with copper, and small amounts of iron, manganese, carbon, and silicon; Monel® is a registered trademark of Huntington Alloys Corporation) and/or may be silver lined.

In one embodiment, delivery of ethylene to reaction vessel 10 is controlled by a mass flow controller 24 within conduit 18, whereas HFP is pumped through conduit 20 as a liquid using an appropriate high pressure liquid pump 26. Optionally, a premixer 28 may be used with reaction vessel 10 and conduits 18 and 20 to pre-mix the reactants prior to conveyance of the reactants into reaction vessel 10.

In some embodiments of the present invention, an oligomerization/polymerization (OP) inhibitor is used to control or prevent oligomerization and/or polymerization from occurring during the reaction. The OP inhibitor may be delivered from a supply tank via a dedicated conduit 32, or alternatively may be delivered along with either or both reactants via conduits 18 and/or 20. A supply device 34, such as a mass flow controller or a pump, depending on the physical nature of the OP inhibitor may be used to devliver the OP inhibitor.

Constant pressure in reaction vessel 10 may be maintained using a back pressure regulator or research control valve (RCV) assembly, schematically shown in FIG. 2 at 36. The reaction may be monitored, at desired intervals, by analyzing exit products using gas chromatography (GC), for example, and/or other analytical methods.

The product TFMCB may be separated from unreacted ethylene and hexafluoropropene via separator 38, and collected continuously after withdrawal form reaction vessel 10 in a cooled vessel 40, for example. Unreacted ethylene and hexafluoropropene may be recycled back to reaction vessel 10 (and/or to another suitable point in the process) via conduit 42. As would be appreciated by one of ordinary skill in the art, various modifications of reaction vessel 10 and its associated components from the depiction shown in FIG. 2 are possible for conducting the reaction as well as for the collection and the separation of the products.

The reaction may be carried out at a temperature as low as 250° C., 300° C., or 330° C., or as high as 400° C., 500° C., or 600° C., or may be carried out within any range defined between any two of the foregoing values, such as 250-600° C., 300-500° C., or 330-400° C. In a specific embodiment, the reaction temperature is between 300 and 350° C.

The reaction may be carried out at a pressure as low as 400 psig, 600 pisg, or 800 psig, or as high as 1200 psig, 1500 psig, or 2000 psig, or may be carried out within any range defined between any two of the foregoing values, such as 400-2000 psig, 600-1500 psig, or 800-1200 psig. In a specific embodiment, the reaction pressure is between 800 and 900 psig.

The ratio of the reactants hexafluoropropene to ethylene present in reaction vessel 10 during the reaction, can range from 1:1 to 1:10, alternatively from 1:1 to 1:6, and still alternatively from 1:1 to 1:3. In a specific embodiment, the ratio is 1:2.

Metal catalysts include nickel and nickel-based alloys such as Monel® alloy, nickel Propak® distillation column packing (size 0.16 or 0.24 inch), nickel alloy 200 (UNS NO 2200, nickel alloy 201 (UNS NO 2201) and nickel alloys of greater than 99% purity. Catalysts can also be in the form of meshes, granules, wires, foams and the like, though will typically be used in the form of distillation column packing.

During the reaction, the synthesis of TFMCB comprises a thermal, catalytic cyclodimerization of hexafluoropropene and ethylene, optionally in the presence of an OP inhibitor to control undesired oligomerization and/or polymerization of the reactants, which would form undesirable by-products. According to the present process, TFMCB may be produced to a high selectivity of about 70-90% as well as a high purity of between 80-90% directly from the reaction of hexafluoropropene and ethylene. Alternatively, if desired, the TFMCB product may itself be further purified, such as by distillation, in subsequent steps to further increase its purity.

A number of OP inhibitors can also be employed to minimize or prevent the oligomerization or polymerization of ethylene and HFP. Exemplary OP inhibitors include terpene, quinone, nitroxyl nitroxyl, hyrdoxylamine based and other inhibitors, such as α-pinene, limonene, terpineol, t-butyl catechol, hydroquinone, napthoqquinone, p-methoxy hydroquinone (MEHQ), N.N-diakylhydroxylamines, 2,2,6,6,-tetramethylpiperidinyl-1-oxl (TEMPO), 2-sec-butyl-4,6-dintrophenol (DNBP) and gas phases inhibitors such as nitric oxide (NO), nitrogen dioxide ($NO_2$), carbon monoxide (CO) and sulphur dioxide ($SO_2$), as well as combinations of the foregoing. The gas phase inhibitors nitric oxide (NO), nitrogen dioxide ($NO_2$), carbon monoxide (CO) and/or sulphur dioxide (SO$_2$) may be added to the reaction mixture as neat gases, or may be diluted with an inert gas such as nitrogen, for example, such that the amount of OP inhibitor used is between 0.01 wt. % and 5 wt. %, for example, or within the ranges set forth below, based on the total weight of the reactant raw materials.

Many of the OP inhibitors are solid and therefore are typically dissolved in a suitable nonreactive solvent, such as dodecane, prior to being pumped into reaction vessel 10 via pump 20, for example. Gaseous, or gas phase, polymerization inhibitors, such as nitric oxide diluted with nitrogen, may be supplied to reaction vessel 10 via mass flow controller 18. Typically, the OP inhibitors are used in low concentration relative to the raw materials, for example, the amount of OP inhibitor used may be as little as 50 ppm, 100 ppm, 200 ppm, or 500 ppm, or as great as 1,000 ppm, 2,000 ppm, or 1 wt. %, based on the weight of the reaction composition in reaction vessel 10, or may be present within any range defined between any two of the foregoing values, such as 100 ppm to 1 wt. %, 200 ppm to 2,000 ppm, or 500 ppm to 1,000 ppm.

In one embodiment, the OP inhibitor is a gas phase inhibitor such as nitric oxide (NO) which, advantageously, may be fed into reaction vessel 10 either neat or as diluted with an inert gas such as nitrogen through a mass flow controller.

II. Production of 2,3,3,3-tetrafluoropropene (HFO-1234yf)

Another aspect of the present invention is directed to a process for making HFO-1234yf and/or vinylidine fluoride (VDF) by converting TFMCB to VDF and/or HFO-1234yf, such as by cracking, and in some embodiments by thermal cracking (hereinafter referred to as "pyrolysis"), in which the TFMCB is held in a reaction zone for a contact time of less than about 10 seconds and at an average temperature of less than about 850° C. to produce (VDF) and/or HFO-1234yf, preferably both VDF and HF-1234yf and even more preferably in a VDF:HFO-1234yf mole ratio of less than about 1.5:1 and not less than about 0.8:1.

In a further embodiment, a process for forming VDF and/or HFO-1234yf is provided including the steps of: (a) providing a stream comprising 1,1,2-trifluoro-2-trifluoromethyl-cyclobutane (TFMCB); and (b) cracking, such as by pyrolyzing, the 1,1,2-trifluoro-2-trifluoromethyl-cyclobutane (TFMCB) for a contact time of less than about 10 seconds and at an average temperature of less than about 850° C. to produce VDF and/or HFO-1234yf, preferably both VDF and HF-1234yf and even more preferably in a VDF:HFO-1234yf mole ratio of less than about 1.5:1 and not less than about 0.8:1.

One embodiment of the pyrolysis reaction according to this aspect of the invention is depicted in Reaction Scheme I below:

Reaction Scheme I:

(Eq. 1)

major proportion by weight or still further alternatively, consisting essentially of, TFMCB. The tubular reactor may be a stainless steel tube placed in a furnace maintained at elevated temperature and passing the TFMCB through the reactor, such as via a continuous operation, at a contact time of less than about 10 seconds, alternatively less than about 5 seconds, to produce a reaction product stream comprising 1234yf and/or VDF.

A quenching operation may be employed to quickly reduce the temperature of the reaction product to halt the pyrolysis reaction, such as for example, introducing the reaction product stream into a cylinder maintained at temperature much lower than the temperature of the heated reaction vessel. In some embodiments no carrier gas (e.g., helium) is present in the reaction stream, which reduces the cost and simplifies the purification of the reaction products. The reaction temperatures may range from 500° C. to 1000° C., alternatively from 750° C. to 850° C.

Although applicants do not intend to be bound by or to any particular theory of operation, it is believed that conducting the pyrolysis reaction in accordance with prior practice, as exemplified for example in the '299 patent, can result poor product yield and/or conversions as a result of, for example, over-cracking of the reactants, which in turn also has the potential disadvantage of resulting in low run times and/or high reactor fouling rates, potentially making such operations not commercially viable. Applicants have unexpectedly found that these and other disadvantages associated with prior operation can be avoided, and substantial and important improvements can be achieved, by operating the pyrolysis reaction within the process ranges described herein.

In certain particular embodiments, the pyrolysis provides a yield in the range of about 80% to about 90%, based on the amount of VDF and HFO-1234yf together, and preferably in a VDF:HFO-1234yf molar ratio of from about 1.5:1 to about 0.8:1. In certain embodiments, the pyrolysis provides a conversion rate of about 70%, based on the conversion of the starting materials.

In certain embodiments, the pyrolysis is conducted in a batch mode. Alternatively, the pyrolysis is conducted in a continuous mode. The process may further include a step of separating the mixture of the compounds HFO-1234yf and vinylidine fluoride, using conventional techniques.

The pyrolysis or cracking of 1,1,2-trifluoro-2-trifluormethyl-cyclobutane (TFMCB) may be conducted continuously at an average temperature of from about 750° C. to about 800° C. in a suitable reactor (e.g., stainless steel or the like) to afford a mixture of both HFO-1234yf and VDF.

Typically, the thermal cracking of the neat cyclobutane compound in a hot tube reactor gave a mixture of 1234yf and VDF in excellent yield (atom efficiency percentage of about 80% to 90%) with a conversion of rate of about 70%. Approximately 3% to 5% of unreacted HFP and ethylene were observed in the product mixture. If desired, this mixture of compounds may be separated using conventional methods.

Since TFMCB is a liquid (bp 67° C.), it is conveniently added to the reactor via a heated mixer operated at about 100° C., which vaporizes the TFMCB. The tube reactor is first flushed with nitrogen and thereafter, neat liquid TFMCB is introduced to the heated zone at a predetermined flow rate, e.g., via a syringe pump or the like.

It should be noted that during the pyrolysis of TFMCB in the examples, both HFP and ethylene were formed, each generated at about 3% to about 5%, between temperatures ranging from 500° C. to 900° C. This ratio did not change, As described herein, one embodiment of this reaction is conducted by introducing into a reaction vessel, such as a heated tubular reaction vessel, a stream including, such as a even when changes were made to the pyrolysis conditions, including: temperature, contact time, and the presence or absence of carrying gases. This discovery was surprising in view of the teachings of the '299 and '407 patents discussed above, which disclosed no HFP and/or ethylene formation in the pyrolysis process.

EXAMPLES

The examples provided below are for illustrative purposes only to demonstrate the continuous production of TFMCB.

General Background for Examples 1-5

A stainless steel pipe reactor (24×1.25 inch or 24×1.0 inch) was packed with Monel (alloy 400, 0.16 inch) or Nickel (alloy 200, size 0.24 inch) Propak® distillation column packing. This tubular reactor was equipped a rupture disk assembly for safety (rated to appropriate pressure) as well as an internal thermal sensor (5 points). The top end of the reactor (vertical orientation) was connected to a pre-mixer, and the bottom end was connected to a back pressure regulator to maintain a predetermined pressure. The tube reactor was heated to the required temperature by either a heating tape or placing the reactor in a furnace. The heated zone of the tubular reactor was 12 inches long in all examples described below. The feed and product mixture were monitored by GC by collecting samples from the respective sample ports. The liquid product, mainly TFMCB, is collected in a stainless steel cylinder attached to the bottom of the reactor and analyzed by GC for purity.

Example 1

Continuous Reaction of Ethylene and HFP with Monel (Alloy 400) Packing

A mixture of ethylene (245 sccm via mass flow controller) and liquid HFP (0.61 ml/minute via liquid pump) was constantly fed to a stainless steel tubular reactor (24×1.25 inch) packed with Monel Propak® at 760-810 psig and 335° C. for 3 hours (contact time, about 10 min). Before the reactants passed to the main reactor they were passed through a premixer (12×0.75 inch with a static mixer) at 150-180° C. Under these conditions, analysis of the exit gases by GC indicated 17% conversion of HFP to TFMCB and 79% selectivity.

Example 2

Continuous Reaction of Ethylene and HFP with Nickel (Alloy 200) Packing

The reaction was carried out in the same manner as in Example 1 except that alloy 200 (nickel) packing was used in place of Monel. Under these conditions, analysis of the exit gases by GC indicated 16% conversion of HFP to TFMCB and 86% selectivity.

Comparative Example 3

Continuous Reaction of Ethylene and HFP with No Catalyst

The reaction was carried out in the same manner as in Example 1 except that no catalyst packing was used. Under these conditions, analysis of the exit gases by GC indicated less than 5% conversion of HFP to TFMCB and 85% selectivity

Example 4

Continuous Reaction of Ethylene and HFP with Monel Packing for 5 Hours

Ethylene (21 g/h) and HFP (84.8 g/h) were continuously fed into a stainless steel tube reactor (24×1.25 inch, heated zone 12 inch) packed with Monel packing for 5 hours at 335° C. and 760-810 psig. The contact time was about 10 minutes. GC analysis of exit gases indicated 14% conversion of HFP to TFMCB. A total of 509 g HFP was passed through the reactor over 5 hours and collected 83 g of liquid product containing 80% TFMCB by GC, with collected yield of 80% based on conversion of HFP.

Example 5

Continuous Reaction of Ethylene and HFP with Polymerization Inhibitors

Ethylene (245 sccm), liquid HFP (0.61 mL/min) and polymerization inhibitor (2,2,6,6,-tetramethylpiperidinyl-1-oxl (TEMPO) in dodecane (500 ppm)) were continuously fed into a stainless steel tube reactor (24×1.25 inch, heated zone 12 inch) packed with Monel packing for 3 hours at 361° C. and 760-810 psig. At the end of the reaction, 80.4 g liquid containing 55% TFMCB was collected.

The foregoing reaction was repeated though using a different polymerization inhibitor, namely, t-butyl catechol in toluene (~500 ppm) as the inhibitor at 349° C. At the end of the reaction 59 g crude product was collected which contained 61% TFMCB.

General Background for Examples 6-8 a) Feed System:

Ethylene was supplied to the reaction from a compressed gas cylinder via pressure difference ($\Delta P$~50 psig) through a Bronkhost™ mass flow controller (MFC). The regulator on the $C_2H_4$ cylinder was set to a pressure of approximately 50 psig greater than the operating pressure. The MFC was connected to the feed manifold with a stainless steel braided line; a valve in the feed manifold isolated ethylene supply when not in use. A second ethylene cylinder was used to pre-pad the system to slightly (10-20 psig) below desired operating pressure which reduced the startup time. Nitric oxide (2% in nitrogen) was supplied to the feed manifold through a regulator and a Bronkhorst mass flow controller (MFC).

Hexafluoropropene (HFP) was fed into the manifold as a liquid via a high performance liquid metering pump (Eldex Optos 2HM). Two, one liter stainless steel cylinders containing HFP (~1000 g each) were padded to ~400 psig with nitrogen. A three way valve allowed the HFP supply to be switched between source cylinders. A Swagelok™ 15 micron filter and a check valve were in line. The inlet tubing to the pump was cooled with a chiller (~0° C.); HFP entered the feed manifold slightly forward of the ethylene and inhibitor entry valve.

The feed manifold entered through a ¾" schedule 80 stainless steel pipe fitted with a static mixer. The static mixer assembly was heated with heat tape to a temperature of 150° C. to 200° C. wrapped with fiberglass fabric insulation to limit heat loss. Single point type "J" thermocouples were inserted into the beginning and end of the static mixer. Temperature data was collected with a HP DataLink system. System pressure was monitored from a 2000 psig stainless steel pressure gauge located in the feed manifold just prior to the static mixer.

b) Reactor System:

Pre-heated feed material exited from the static mixer and flowed towards the vertical reactor. The reactor is a 1" schedule 80 stainless steel pipe that is 24" long. All pipe fittings used were schedule 80. As a safety measure, at the top of the reactor was equipped with a ½" Inconel 1500 psig rupture disk. All fittings, pipe, tubing and equipment were rated for pressures above 1500 psig.

The reactor was packed with 154 cm$^3$ of Alloy 200, 0.24" Pro-Pak® protruded metal packing. The active zone of the thermocouple is in the 154 cc catalyst bed. The interior temperature readings in the tube reactor were collected via a HP DataLink system connected to a 5 point type "J" thermocouple (36"×¼" stainless steel) with sensors at 3" apart along the catalyst bed (½", 3", 6", 9" and 12", respectively). The catalyst was held in place small amount of nickel mesh at the top and bottom of the catalyst bed. The reactor was heated to and maintained at the desired temperature by heat tapes which were wrapped with fiberglass fabric to limit heat loss. There was a ¼" Swagelok™ ball valve at the bottom of the reactor that serves as a drain valve. This was used only during maintenance and was kept closed at all other times. The pressure in the reactor was controlled/maintained with an Equilibar™ diaphragm type back pressure regulator (BPR).

c) Product Collection:

Reaction products exited via BPR and entered ½" by 30" jacketed stainless steel column packed with stainless steel Pro-Pak®. The column was cooled to 0° C.; heavier byproducts condensed and was collected in 250 cc stainless steel doubled ended cylinder which can be isolated and drained during the reaction if desired. Vapor continues on to a 1 gallon dry ice trap equipped with a pressure gauge and dip tube which extends to the half way point of the cylinder. Most of the TFMCB and HFP were collected here; a second trap (1L with pressure gauge) collected any HFP that escaped from the first one. Typically, ethylene was vented out or can be condensed in a liquid nitrogen trap.

d) Sampling:

Vapor samples were taken at two separate points. A sample of feed mixture could be taken after the static mixer but just before the reactor. A pair of ¼" stainless steel Swagelok™ ball valves were used in sequence to trap a small amount of material between the two valves. The second valve was opened to vent the material into a 300 cubic centimeter stainless steel cylinder.

Reaction products in vapor phase were collected for analysis a stainless steel cylinder with a digital pressure gauge is installed in a sampling loop after the BPR. When desired, a ¼" stainless steel Swagelok™ ball valve can be closed to direct the outflow through the sample cylinder. The exit valve on the sampling cylinder was closed and the cylinder was filled until the pressure reaches ~20 psig. Then upstream valve was closed and the ¼" stainless steel Swagelok™ ball valve opened again to restore the flow path.

e) Analytical—GCs:

The gas phase samples were analyzed with a Cryo GC [model HP5890A with a FID, and Restek™ RTX1 column, 105 m. long; operating conditions: initial temperature −55° C., ramps 15° C./min 150° C. (no hold) and 25° C./min to 180° C. (hold for 5 min) and run time, 29.37 min]. Liquid samples of TFMCB were run on a normal GC [model HP5890A with a FID and Restek™ RTX1 column 105 m long; conditions were as follows: initial temperature=60° C. for 1 min, ramp 7° C./min to 200° C. (hold @ 200° C. for 5.5 min) and total run time=27.5 minutes]. Note that the gas phase GC components were normalized/calibrated to volume/mole % by BRL analytical department. GC purity % of TFMCB in the crude liquid product was validated gravimetrically (distillation) and by NMR ($^1$H and $^{19}$F) analyses.

Example 6

Continuous Reaction of HFP and Ethylene in the Absence of Oligomerization/Polymerization (OP) Inhibitor Hexafluoropropene (HFP) and ethylene were passed through a heated tube over a catalyst bed [catalyst=alloy 200, temperature=343° C., pressure=800-850 psig, HFP to ethylene ratio=1:2 and contact time=10 min] with no polymerization inhibitor continuously for 10 hrs. Under these conditions, TFMCB was produced in 84% selectivity with a conversion rate of 34%; mass balance within 3% accuracy was observed.

Example 7

Continuous Reaction of HFP and Ethylene in the Presence of Polymerization Catalyst Hexafluoropropene (HFP) and ethylene were passed through a heated tube over a catalyst bed [catalyst=alloy 200, temperature=330° C., pressure=800-850 psig, HFP to ethylene ratio=1:2 and contact time=15 min] with ologomerization/polymerization (OP) inhibitor (nitric oxide) continuously for 3 and 10 hours, respectively. Under these conditions, selectivity ranged from 91-94% with conversion rate 9 to 11%. Thus, selectivity can be improved with use of a gas phase oligomerization/polymerization (OP) inhibitor.

Example 8

Continuous Reaction of HFP and Ethylene—Continuous Production of TFMCB for 4.5 Days Hexafluoropropene (HFP) and ethylene were passed through a heated tube over a catalyst bed [catalyst=alloy 200, temperature=322° C., pressure=840-850 psig, HFP to ethylene ratio=1:1.5 and contact time=12 min] with oligomeriztion/polymerization (OP) inhibitor (nitric oxide) continuously for 4.5 days; TFMCB was obtained in 91% selectivity with a conversion rate of 12%.

Comparative Example 9

Non-Catalytic Batch Production of TFMCB

In a 1000-mL stainless steel cylinder was charged with 0.6 g t-butyl catechol, the cylinder is evacuated with nitrogen three times. Next, 52.0 g of HFP and 11.6 g of ethylene (mole ratio 1/1.19) were condensed into the cylinder. The cylinder was heated to 242° C. to 250° C. for 72 hours, and the inside pressure dropped from 600 psi to 500 psi at the end of reaction. Unreacted HFP and ethylene were recovered in a separate cylinder (39.6 g), and the product of 19.6 g was withdrawn from the reactor by vacuum. GC analysis showed 96.58% pure TFMCB.

Comparative Example 10

Non-Catalytic Batch Production of TFMCB

A 2-L stainless cylinder was charged with 1.01 g of t-butyl catechol, and the cylinder is evacuated with nitrogen three times. Next, 50.0 g of HFP and 56.5 g of ethylene were condensed into the cylinder. The cylinder was heated to 320° C. to 329° C. for one hour, and the inside pressure dropped from 700 psi to 500 psi at the end of reaction. Unreacted HFP and ethylene were recovered in a separate cylinder (75.8 g), and the TFMCB product (29.4 g) was decanted from the reactor.

GC analysis showed 94.34% purity (46.2% yield based on HFP). Further distillation through a column gave 99.8% pure 1,1,2-trifluoro-2-trifluoromethyl-cyclobutane (TFMCB), $^1$H-NMR (CDCl$_3$) 2.62 ppm (m, 1H), 2.45 ppm (m, 2H), 2.24 ppm (m, 1H); $^{19}$F-NMR (CDCl$_3$) −80.70 ppm (dt, J=9.3, 2.5 Hz, CF$_3$), −101.0 ppm (dm, J=212.9 Hz, 1F), −114.73 ppm (dtm, J=211.9, 16.2 Hz, 1F), −176.37 ppm (m, 1F).

Comparative Example 11

Non-Catalytic Batch Production of TFMCB

A 2-L stainless cylinder was charged with 1.10 g of t-butyl catechol, and the cylinder is evacuated with nitrogen three times. Next, a calculated amount of HFP and ethylene were condensed into the cylinder. The cylinder was heated to designated temperature for various time periods. The results were listed in Reaction Table I below.

REACTION TABLE I

| Entry | HFP/Ethylene ratio | Temperature/ ° C. (time/h) | TFMCB Yield % (based on HFP) | Product selectivity % |
|---|---|---|---|---|
| 1 | 1.05/1.0 | 250 (72 h) | 15.4 | 96.6 |
| 2 | 1/1.19 | 242 (72 h) | 26.8 | 96.6 |
| 3 | 1/1.48 | 238 (120 h) | 30.5 | 95.0 |
| 4 | 1/1.97 | 256 (72 h) | 39.6 | 97.6 |
| 5 | 1/3.0 | 350 (19 h) | 89.6 | 77.4 |
| 6 | 1/3.35 | 375 (4 h) | 77 | 74.8 |
| 7 | 1/3.0 | 400 (1.2 h) | 110% yield (some oligomer of ethylene) | 58.4 |
| 8 | 1/0.9 | 400 (1 h) | 69 | 56.9 |
| 9 | 1/3.0 | 365 (3 h) | 90.8 | 84.8 |
| 10 | 1/3.0 | 370 (1.5 h) | 92.9 | 78.0 |
| 11 | 1/3.0 | 320-330 (5 h) | 97.9 | 91.4 |
| 12 | 1/6.17 | 320-331 (1 h) | 66.8 | 94.1 |

Comparative Example 12

Non-Catalytic Batch Production of TFMCB

A one gallon stainless cylinder was charged with 60 mg of t-butyl catechol (200 ppm), and the cylinder is evacuated with nitrogen three times. Next, 140.7 g of HFP and 159.0 g of ethylene (mole ratio 1/6.05) were condensed into the cylinder. The cylinder was heated to 320° C. to 329° C. for one hour, and the inside pressure dropped from 800 psi to 600 psi at the end of reaction. Unreacted HFP and ethylene were recovered in a separate cylinder (174.5 g), and the product of 121.7 g was decanted from the reactor. GC analysis showed 78.10% of TFMCB, and 21.40% of side products from ethylene oligomers by GC and GCMS analysis.

Example 13

Pyrolysis of TFMCB

Pyrolysis of distilled TFMCB (495 g, 99.6%) was carried out in a heated stainless pipe reactor in a furnace (see Table II). The reactor was heated to and maintained at 800° C. for 30 minutes to equilibrate and was flushed with nitrogen. Liquid 1,1,2-trifluoro-2-(trifluoromethyl)-cyclobutane was introduced to the heated zone (100° C.) with a programmed syringe pump.

Once the flow of cyclobutane was started, the nitrogen flow was switched off and the pyrolysis was conducted in a continuous mode. The resulting pyrolysis products were collected in a cooled 1 gallon stainless steel cylinder. GC monitoring of products were done at the beginning and end of the reaction. Details are summarized in Table II below:

TABLE II

Scale Up Summary

| Item | Description |
|---|---|
| Reactor | Stainless steel (0.375″ × 12″); Volume of heated zone = 10.85 cm$^3$ |
| Amount of cyclobutane used | 495.5 g (99.6% GC) |
| Temperature | 800° C. |
| Duration of pyrolysis | 7.83 h |
| Flow rate | 0.74 mL/min (liquid), 130 mL/min (vapor) (or 1.03 g/min) |
| Total products collected | 485.5 g |
| Mass balance | Mass loss = 495.5 − 485.5 = 10 g (2%) (Recovery = 98%) |
| Collection vessel/pressure | 1 gal SS cyl (~200-300 psi at RT); cooled by Liq N$_2$ while collecting. |
| Contact time (CT) | 5 sec [CT = Volume of heated zone cm$^3$/vapor flow rate in sccm] |
| Conversion | 70% |
| Yields | 1234yf (157.2 g, 81%); VDF (105.9 g, 97%) |

Conditions: temperature range ~700°-850° C.;
Contact time ~1 to 60 sec range.

As shown in Table II, the laboratory scale reactor was made from stainless steel and had dimensions of 0.375 inches in diameter and a length of 12 inches, providing a heating zone of 10.85 cm$^3$. As indicated, the flow rate of the TFMCB provided a contact time of 5 seconds for the pyrolysis reaction. The collection vessel was also made from stainless steel and was cooled with liquid nitrogen during the collection of the reaction product mixture.

For production purposes, the reactor will be much larger, using suitable constructions materials for conducting the pyrolysis reaction on much greater amounts of TFMCB. Reaction temperatures may vary from those employed in the laboratory scale reactor. It is anticipated that the product composition of 1234yf/VDF to HFP/ethylene will not change, but the TFMCB conversion will be affected by changes in the operational temperatures. No carrier gas is expected to be used in a production plant. Finally, in production processing, the collection vessel will be much larger, and cooling will be provided by alternate means, such as cold water. In a production plant, it is anticipated that the product gas out of the reactor would be compressed into a pressurized storage vessel before distillation or further processing.

Comparative Examples 14A & 14B

1A. The purified TFMCB (3.0 g) from Example 13 was passed through a heated stainless tube reactor at 800° C. at 0.5 ml/min. The reaction tube had a diameter of 1.5 cm with a reaction zone length of 13.0 cm, which was filled with 6.8 g Inconel 625 mesh. The contact time with helium carrier gas of 66.7 ml/min was 14.1 sec, and 3.0 g of product gas was collected. GC analysis showed 3.8% ethylene, 48.7% VDF, 3.3% HFP, and 44.2% 1234yf.

1B. The reaction temperature was lowered to 750° C., 3.79 g of TFMCB was passed through the tube at 32.4 sec contact time. 3.78 g of product was recovered. GC analysis showed 3.8% ethylene, 48.9% VDF, 3.2% HFP, and 44.1% 1234yf.

Example 15

A number of reactions were carried out at various temperatures and contact times. Typically, the reactions were carried out by passing neat vaporized 1,1,2-trifluoro-2-(trifluoromethyl)-cyclobutane through a stainless tube/pipe reactor placed in a heated furnace. These results are shown below in Table III.

TABLE III

Pyrolysis of neat 1,1,2-trifluoro-2-(trifluoromethyl)cyclobutanes

| Run # | 41923- | T (° C.) | cyclobut. Feed Used (g) | Flow rate Liq. Flow (mL/min) | Vap Flow (mL/min) | CT (sec) | Products -mixture Vol %* by GC |  |  |  |  |  |
|---|---|---|---|---|---|---|---|---|---|---|---|---|
|  |  |  |  |  |  |  | Ethylene | VDF | HFP | 1234yf | Feed | Others |
| 11** | 32-4 | 700 | 31.80 | 0.20 | 35.41 | 18.4 | 5.01 | 60.17 | 2.29 | 30.18 | 0.05 | 2.3 |
| 12 | 33-1 | 750 | 4.78 | 0.76 | 133.67 | 4.9 | 3.72 | 48.74 | 3.23 | 42.12 | 1.68 | 0.51 |
| 13 | 33-2 | 800 | 5.23 | 1.25 | 219.38 | 3.0 | 3.69 | 46.48 | 3.09 | 40.54 | 5.76 | 0.44 |
| 14 | 33-3 | 750 | 3.93 | 0.94 | 164.85 | 3.9 | 3.63 | 47.27 | 3.18 | 41.52 | 3.83 | 0.57 |
| 15 | 33-4 | 750 | 5.45 | 1.20 | 211.03 | 3.1 | 3.68 | 45.93 | 3.15 | 40.88 | 5.9 | 0.46 |
| 16 | 33-5 | 750 | 4.32 | 0.78 | 135.91 | 4.8 | 3.69 | 47.58 | 3.29 | 43.02 | 0.02 | 2.4 |
| 17 | 33-6 | 800 | 3.97 | 0.67 | 117.55 | 5.5 | 3.8 | 48.64 | 3.29 | 43 | 0.68 | 0.59 |
| 18 | 33-7 | 800 | 2.98 | 0.53 | 93.75 | 6.9 | 3.68 | 48.23 | 3.31 | 43.78 | 0.21 | 0.79 |

*volume % based on calibration by analytical dept. Tube Reactor: SS tube; ⅜" diameter, volume of heated zone 10.85 cm³.
**Done at 31.8 g scale and products collected 32 g in a cylinder.

As shown in Table III, the ratio of VDF to HFP was relatively constant and there remained about 2-5% of unreacted HFP and ethylene.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

The invention claimed is:

1. A process for producing 1,1,2-trifluoro-2-(trifluoromethyl)cyclobutane (TFMCB), comprising the following steps:
   introducing hexafluoropropene and ethylene into a reaction vessel; and
   reacting the hexafluoropropene and ethylene in the reaction vessel in the presence of at least one oligomerization/polymerization (OP) inhibitor and at least one metal catalyst.

2. The process of claim 1, wherein the process is a continuous process and further comprises the additional steps, following the reacting step, of:
   removing TFMCB product from the reaction vessel; and
   repeating said introducing, reacting and removing steps (a) through (c).

3. The process of claim 1, further comprising the additional steps, following the reacting step, of:
   removing at least one of unreacted hexafluoropropene and unreacted ethylene from the reaction vessel; and
   recycling the at least one of unreacted hexafluoropropene and unreacted ethylene back into the reaction vessel.

4. The process of claim 1, further comprising the additional steps, following the reacting step, of:
   removing unreacted hexafluoropropene and unreacted ethylene from the reaction vessel; and
   recycling the unreacted hexafluoropropene and unreacted ethylene back into the reaction vessel.

5. The process of claim 1, wherein the metal catalyst is selected from the group consisting of nickel and nickel-based alloys.

6. The process of claim 1, wherein the oligomerization/polymerization (OP) inhibitor comprises at least one gas phase compound selected from the group consisting of nitric oxide (NO), nitrogen dioxide ($NO_2$), carbon monoxide (CO) and sulphur dioxide ($SO_2$).

7. The process of claim 1, wherein the oligomerization/polymerization (OP) inhibitor is 2,2,6,6-tetramethylpiperidinyl-1-oxl.

8. The process of claim 1, wherein the oligomerization/polymerization (OP) inhibitor is selected from the group consisting of catechol and catechol derivatives, terpenes, quinones and combinations thereof.

9. The process of claim 1, wherein the oligomerization/polymerization (OP) inhibitor is present at from about 50 ppm to about 2,000 ppm by weight based on the total weight of the reaction composition in the reaction vessel.

10. The process of claim 1, wherein the oligomerization/polymerization (OP) inhibitor is present at from about 500 ppm to about 1,000 ppm based on the total weight of the reaction composition in the reaction vessel.

11. The process of claim 1, wherein the reacting step is conducted at a pressure between 600 psig and 1500 psig.

12. The process of claim 1, wherein the reacting step is conducted at a pressure between 800 psig and 1200 psig.

13. The process of claim 1, wherein the reacting step is conducted at a temperature between 300° C. and 500° C.

14. The process of claim 1, wherein the reacting step is conducted at a temperature between 300° C. and 400° C.

15. The process of claim 1, wherein during the reacting step, the hexafluoropropene and ethylene are present at a molar ratio of from 1:1 to 1:6.

16. The process of claim 6, wherein the metal catalyst is selected from the group consisting of nickel and nickel-based alloys.

17. The process of claim 5, wherein the oligomerization/polymerization (OP) inhibitor comprises at least one gas phase compound selected from the group consisting of nitric oxide (NO), nitrogen dioxide ($NO_2$), carbon monoxide (CO) and sulphur dioxide ($SO_2$).

18. The process of claim 17, wherein the oligomerization/polymerization (OP) inhibitor is 2,2,6,6-tetramethylpiperidinyl-1-oxl.

19. The process of claim 17, wherein the oligomerization/polymerization (OP) inhibitor is selected from the group consisting of catechol and catechol derivatives, terpenes, quinones and combinations thereof.

20. The process of claim 19, wherein the oligomerization/polymerization (OP) inhibitor is present at from about 50 ppm to about 2,000 ppm by weight based on the total weight of the reaction composition in the reaction vessel.

* * * * *